United States Patent [19]

de Nijs

[11] Patent Number: 4,596,576
[45] Date of Patent: Jun. 24, 1986

[54] RELEASE SYSTEM FOR TWO OR MORE ACTIVE SUBSTANCES

[75] Inventor: Henrik de Nijs, Oss, Netherlands

[73] Assignee: Akzo N.V., Arnhem, Netherlands

[21] Appl. No.: 782,433

[22] Filed: Oct. 1, 1985

[30] Foreign Application Priority Data

Oct. 12, 1984 [NL] Netherlands ............... 8403120
Nov. 29, 1984 [NL] Netherlands ............... 8403626

[51] Int. Cl.⁴ ............................................. A61F 5/46
[52] U.S. Cl. .................................... 604/892; 128/127
[58] Field of Search ............... 604/892, 891, 890, 285; 128/127, 130, 131, 132

[56] References Cited

U.S. PATENT DOCUMENTS

| | | | |
|---|---|---|---|
| 4,237,885 | 12/1980 | Wong et al. | 604/892 |
| 4,286,587 | 9/1981 | Wong | 604/892 X |
| 4,304,232 | 12/1981 | Michaels | 604/892 |
| 4,526,578 | 7/1985 | Wong | 604/892 |

*Primary Examiner*—John D. Yasko
*Attorney, Agent, or Firm*—Abelman Frayne Rezac & Schwab

[57] ABSTRACT

The present invention relates to a release system for the simultaneous release of two or more active substances, which system consists of two or more reservoirs which are each separately encased or surrounded by a wall which is permeable to the active substance, the encased reservoirs then being assembled together so that one release system is obtained.

4 Claims, 6 Drawing Figures

RELEASE SYSTEM FOR TWO OR MORE ACTIVE SUBSTANCES

The present invention relates to a release system for the simultaneous release of two or more active substances, which system consists of two or more reservoirs which are each separately encased or surrounded by a wall which is permeable to the active substance, the encased reservoirs then being assembled together so that one release system is obtained.

Such a release system is known from U.S. Pat. Nos. 3,995,633 and 3,995,634, where separate, preferably spherical or cylindrical, reservoirs containing different active substances are assembled in specially constructed holders. Apart from the fact that the release systems described in these patent specifications are not easy to manufacture from the point of view of the production technology, diffusion or, more generally, transport of one or more active substances from the reservoirs to the holder, which is preferably made of polysiloxane (Silastic), takes place, especially if a system is stored. As a result, the abovementioned release pattern undergoes a slow change.

Especially in the case of the release of two or more active substances this problem is increasingly important in that the preset fixed release ratio between the active substances in question is seriously affected thereby.

Such a release system is also described in U.S. Pat. No. 4,237,885, where a tube or coil of polymeric material is divided into portions by means of a plurality of "spacers" provided in the tube, after which each of the separate tube portions is filled with a different active substance and the two ends of the tube are subsequently connected to one another by some method or other. In this release system, however, transport (diffusion) of active material from one reservoir to the other takes place through the wall of the tube, especially upon prolonged storage. Moreover, the suggested coiling of the tube into a plurality of turns, whereby several parts of the tube come into contact with other parts of the tube, contributes to a constantly progressing diffusion of the active substances into each other's reservoirs. In this release system also, the preset fixed release ratio between the active substances in question will change over a period of time.

Release systems which over a lengthy period release two or more active substances in a fixed constant ratio to one another are extremely useful for certain applications. For example, in the field of contraception, extensive use is made of the simultaneous administration of an agent having a progestative action and an agent having an oestrogen action, preferably in a fixed ratio.

The simultaneous introduction of these two drugs into one reservoir can however only purely accidentally lead to the desired release ratio. In fact, the release per unit time is determined solely and exclusively by the solubility of the active substance in the material—frequently polymeric material—which forms the wall of the reservoir and by the diffusion coefficient of the active substance in that wall. In this type of release system, in fact, the choice of the material of the reservoir wall also already determines the release ratio of the active substances contained in the reservoir.

Contraception 28(4), 315, 1983 (see Table 1 on page 317) describes the release per unit time of a number of progestative substances and an oestrogenic substance (oestradiol) from one particular reservoir. When laevonorgestrel and oestradiol are simultaneously introduced into one reservoir, the release ratio of the said two steroids per unit time is found to be roughly 3:2; the release ratio of norethisterone and oestradiol is found to be about 5:1, that of medroxyprogesterone acetate and oestradiol about 4:1 and that of megestrol acetate and oestradiol about 10:1.

Though theoretically it is possible to choose from among a very large variety of polymeric materials, it is found in practice that only a small number of polymers seem to be capable of functioning as a wall, permeable to the active substance, of a reservoir. Not only does the medical use impose certain requirements on the polymer but in addition a very large number of polymers are unsuitable in that, for example, they possess insufficient rigidity, are insufficiently inert etc.

In most cases one is therefore forced to choose a release system with a plurality of separate reservoirs as a release system which is capable of releasing two or more active substances in a particular ratio.

It is true that the two patent publications mentioned above describe release systems with a plurality of reservoirs, but none of the release systems described—certainly if they have been kept or stored for some time before being used—gives a substantially constant release ratio between two active substances contained in the system over a lengthy period of time. Diffusion or transport of the active material from one reservoir to the other and/or of both active substances into a polymer used as the holder appears in all cases to have a surprisingly greater adverse effect on the ratio of the active substances in question which has been preselected and regarded as the most ideal. Accordingly, a release system which is simple to construct and does not suffer from the disadvantages described above has been sought.

There has now been found a release system of the type mentioned in the introductory part of this patent Specification, which is characterised in that the encased reservoirs are substantially tubular and at least one end of such a tubular reservoir is attached to the end of another tubular reservoir by means of a plug or stopper which does not permit transport of the active substances either by diffusion or by any other method, there being no contact between the walls of the reservoirs involved.

Preferably, the other ends of the tubular reservoirs are similarly connected to one another by means of one (or more) of the abovementioned stoppers or plugs, so that the release system becomes ring-shaped.

Within the scope of the present invention, reservoir means a substantially tubular reservoir which possesses a wall which is permeable to the active substance and which contains the active substance in the part which is encased by the wall. At least one, but preferably both, ends of the tubular reservoir is or are adapted for attachment of a plug or stopper according to the invention.

The reservoir may be entirely or partially filled with the active substance. However, the active substance is preferably contained in a liquid or solid which permits transport of the active substance to the wall of the reservoir and in any case transports (whether by diffusion or by some other means) the active material no less rapidly than the rate of transport of the active material through the wall of the reservoir. The permeability of the wall to the active substance should at all times determine the rate of release of the active material.

As examples of particularly suitable liquids or liquid-like substances which possess good permeability for most active substances and can therefore ensure rapid transport of the drug to the wall of the reservoir there may be mentioned vegetable or animal oils, polyalkylene glycols such as polyethylene glycol (400–6000) and polypropylene glycol (500–2000), certain buffers and also water or water mixed with the abovementioned polyalkylene glycols.

Examples of suitable solids which can be used for the above purpose are polymers, such as polysiloxanes, impregnated with the active substance or microporous polymers filled with the active substance and optionally with other auxiliaries, such as microporous polyethylene or microporous polypropylene.

The expressions "active substance" and "active material", as used above, in general encompass all substances which—if administered in an effective quantity—bring about an advantageous effect. This definition of active material or active substance thus covers, for example, pesticides, herbicides, insecticides, anti-oxidants, disinfectants, cosmetics and above all biologically active substances (or drugs). Since a very useful application of the present invention is in the field of contraception, active substances preferably means substances (mostly steroids) which influence fertility and in particular the combination of progestative and oestrogenic substances.

It is in particular of essential importance that the progestative substance and the oestrogenic substance are released simultaneously and in a fixed ratio to one another over a lengthy period. Examples of progestative substances which can be used within the scope of the present invention are: 3-keto-desogestrel, desogestrel, (laevo)norgestrel, norethindrone, norethynodrel, norgesterone, lynestrenol, norgestrienone and progesterone.

Examples of oestrogenic substances are: α-oestradiol and esters thereof, oestrone, ethinyloestradiol and 17-ethinyloestradiol-3-methyl-ether.

The wall of the tubular reservoirs is preferably made of a polymeric material which in general has no harmful or adverse effect on the medium in which the system is used. For the release of biologically active material and especially for the abovementioned use as a contraceptive, the polymer to be used must moreover be suitable for use in man or animals.

Polymers which can be used for these purposes are generally known, so that in fact reference may be made to the literature as regards this aspect. Examples of suitable polymers are polysiloxanes, polyurethane, polyethylene, ethylene/vinyl acetate copolymers, cellulose, copolymers of polystyrene, polyacrylates and various types of polyamides and polyesters. The abovementioned polymers can and may also be used in a porous or microporous form. In the last-mentioned group of polymers, the transport of the active material in the main takes place through the pores of the polymer and not—or to a lesser extent—through diffusion.

The plug or stopper which connects two tubular reservoirs according to the invention is made of an inert material which in no manner permits any transport of active material. Examples of impermeable material are metals, such as gold, silver or silver alloys, glass or ceramic material and elastomers which are necessarily encased in a metal or glass coating.

The stopper or plug according to the invention completely seals the tubular reservoir so that no active material can leach out through a poor connection between the reservoir and the stopper or plug. If desired, an adhesive can be used for better sealing or better adhesion of the stopper to the reservoir; for medical application the adhesive must of course be suitable for such applications.

The plug or stopper according to the invention can have any desired shape provided that the two tubular reservoirs in question are hermetically sealed and that with the plug or stopper to be used these reservoirs cannot in any way whatsoever come into contact with one another.

FIG. 1 shows a stopper or plug (1) according to the invention which connects reservoirs A and B to one another. The plug possesses a projection (4) which prevents the walls (2) and (3) of the reservoirs A and B from coming into contact with one another. The projection (4) preferably has a "length" which roughly corresponds to the thickness of the walls of the reservoirs.

Figure 1:
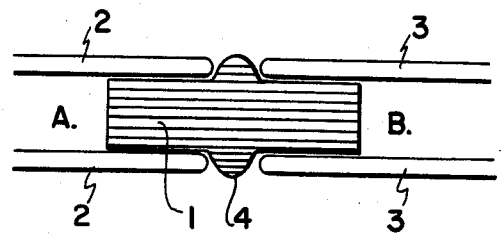
Figure 2:
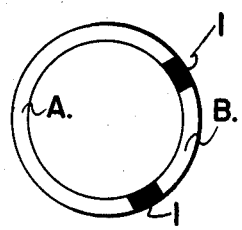
FIG. 2 shows a ring consisting of two reservoirs, wherein the reservoirs A and B are connected to one another by two plugs (1).
Figure 4:
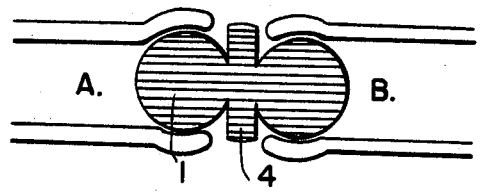
FIG. 4 shows a different embodiment of the stopper or plug.
Figure 3:
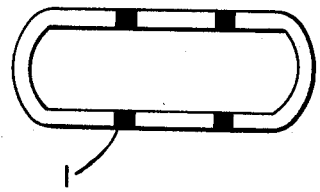
FIG. 3 shows an elliptical release system consisting of four different reservoirs.

As already mentioned earlier, a drug release system which can be used for contraceptive purposes is obtained by connecting two or more tubular reservoirs by means of the plugs or stoppers according to the invention in such a way that a ring-shaped release system results. This ring must, in respect of rigidity and dimensions, be suitable for use as a vaginal ring. If desired a so-called placebo reservoir can be incorporated in order to obtain a ring of a particular diameter. This placebo reservoir of course does not contain any active substance so that no release of active material from this reservoir can take place.

A variant which is considered to fall within the essential nature of the invention consists of a ring-shaped release system wherein one tubular reservoir filled with active substance is attached to a tubular placebo reservoir by means of two plugs according to the invention.

Furthermore, it is self-evident that the afore defined reservoirs do not necessarily contain only one active substance. If desired, more than one active substance may be present in a single reservoir without affecting the essence of the invention.

As already pointed out the preferred drug delivery system for contraceptive purposes is a vaginal ring according to this invention in which a progestative substance and an oestrogenic substance are contained in separate drug-reservoirs.

In general, it is considered undesirable to expose the vaginal tissue to the local activity of an oestrogenic substance for a too long period. It is therefore preferred to add an anti-oestrogenic substance to the same reservoir, in which the oestrogenic substance is present, in order to neutralise the local effects of the oestrogenic substance.

Anti-oestrogenic substances are generally known; the preferred anti-oestrogenic substance has a systemic progestative effect.

In other words a more preferred drug delivery system is a vaginal ring according to the instant invention, in which one reservoir contains a progestative substance and (one of) the other reservoir(s) contains both an oestrogenic and an anti-oestrogenic substance.

The release ratio of the two active substances in the release system according to the invention can be varied by:

making the walls of the tubular reservoir from different materials, making the walls of the tubular reservoirs from the same material but varying the thickness of the wall and making the walls of the reservoirs from the same material (including the same thickness) but varying the length of the reservoir.

EXAMPLE 1

0.5% by weight of Dow Corning catalyst M were added to a mixture consisting of 97.7% by weight of medical grade Silastic, type 382, 0.1% of titanium dioxide, 0.2% of ethinyloestradiol and 2% of 3-keto-desogesterol.

The viscous mixture was then forced into a (medical grade) Silastic tube having an external diameter of 4.8 mm and an internal diameter of 2.6 mm. The mixture hardened very rapidly under the influence of the catalyst. 16 cm of the filled tube were subsequently bent into a ring by cementing the two ends to one another by means of medical grade Silastic adhesive type A.

Figure 5:
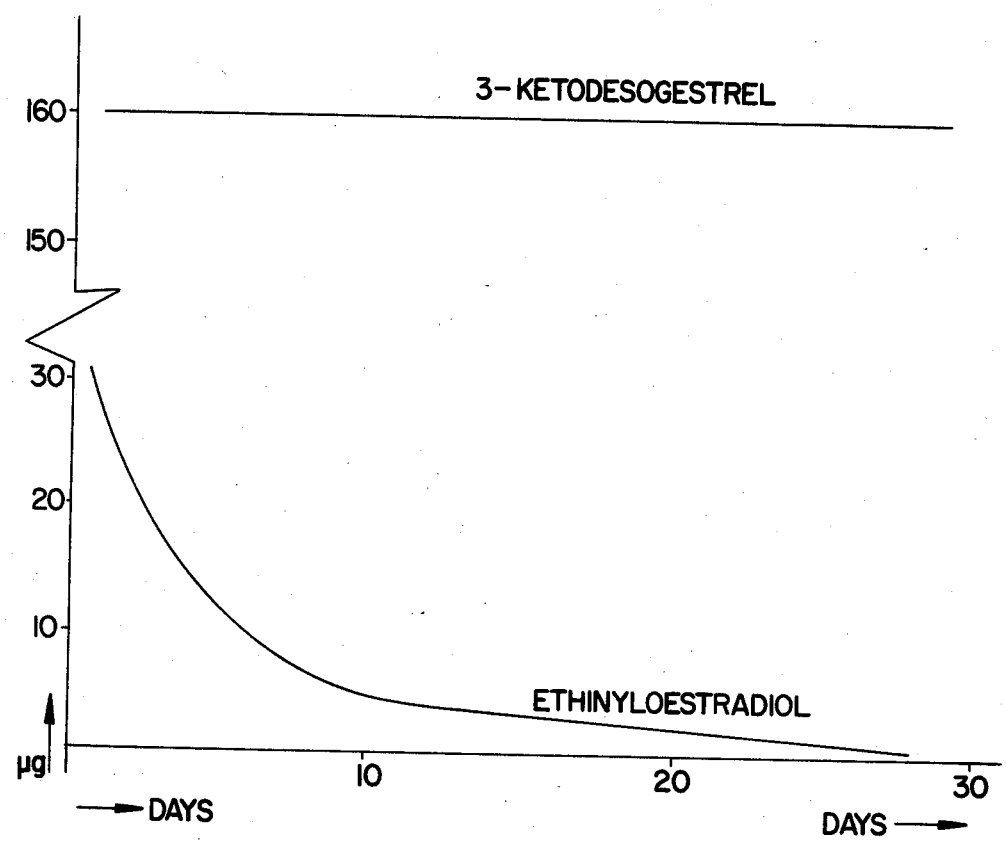

The release characteristics of the progestative and the oestrogenic substance in this single-reservoir system are shown in FIG. 5.

EXAMPLE 2

In an identical manner to that in Example 1, a Silastic tube was filled with a mixture of 98.4% of Silastic type 382, 0.1% of titanium dioxide and 1.5% of 3-keto-desogesterel and another tube was filled with an analogous mixture wherein 1.5% of 3-keto-desogesterol was replaced by 1.5% ethinyloestradiol.

Using two small polymeric (Silastic) stoppers, 15 cm of the tube filled with 3-keto-desogesterol were coupled to 1.5 cm of tube filled with ethinyloestradiol so that a ring was formed.

After a storage period of 3 months at room temperature, an oestrogen release pattern was found which was virtually identical to the oestrogen released pattern shown in FIG. 5.

EXAMPLE 3

Two tubes were produced in an identical manner to that described in Example 2, one being filled with 3-keto-desogesterel and the other with ethinyloestradiol. Using two glass plugs (of the type shown in FIG. 1) and Silastic medical grade adhesive, type A, the two tubes were combined into a ring, in the manner shown in FIG. 1.

Figure 6:
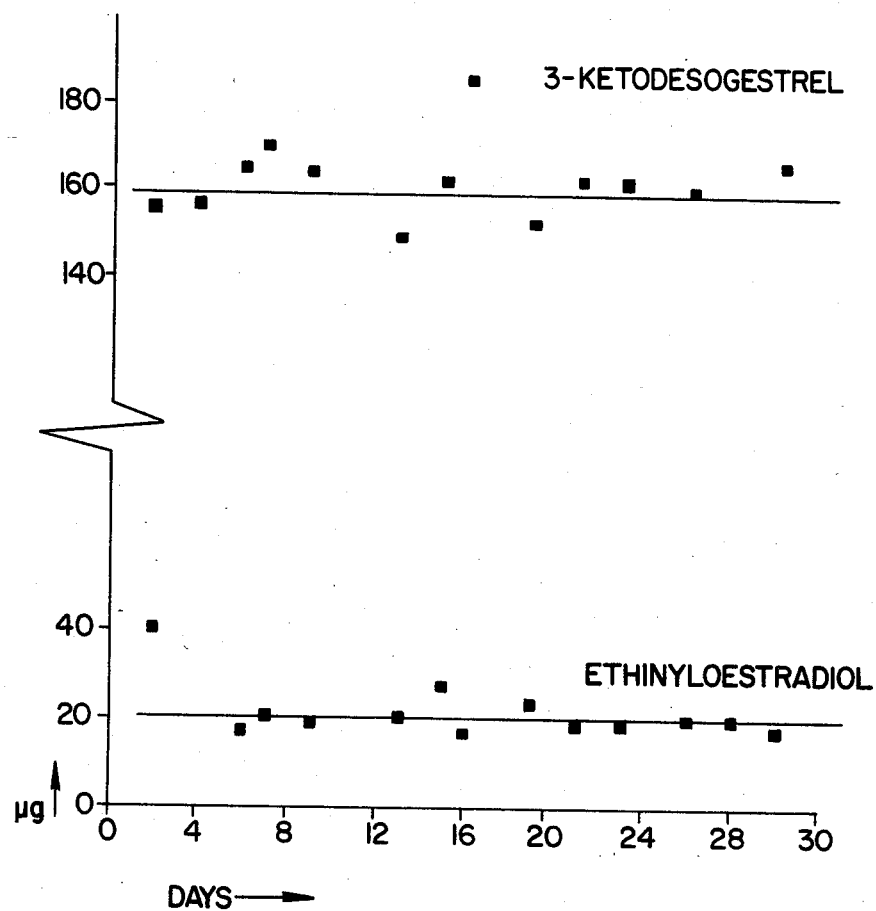

After a storage time of 3 months at room temperature, the ring showed a release pattern as reproduced in FIG. 6.

The system according to the invention, even after several months' storage, still showed a linear release of 3-keto-desogesterel and of ethinyloestradiol in a substantially constant ratio of 8:1.

EXAMPLE 4

The same "two-reservoirs" ring system as described in Example 3 was produced, with the difference that only 1.0 cm instead of 1.5 cm of tube containing ethinyloestradiol was used.

The release pattern of this ring is identical to that shown in FIG. 6, with the difference that the release level of ethinyloestradiol is 11 μg per day instead of 20 μg per day.

Accordingly, with this vaginal ring a constant release ratio of 14 to 15:1 can be obtained.

EXAMPLE 5

A "three-reservoirs" ring system was also produced in the same manner as that described in Example 3, the system consisting of a tube of 7.5 cm of 3-keto-desogestrel, a tube of 1.5 cm filled with ethinyloestradiol and a tube of 7.5 cm filled with placebo (the content of the placebo tube was identical to the content of the two other tubes, except that the active constituent was omitted).

In this system, the placebo tube is needed to obtain a ring having a useable diameter. The release pattern of this ring was identical to that of FIG. 6, except that the level of 3-keto-desogestrel released was roughly 80 μg per day.

Accordingly, in this system, the constant ratio of progestative substance/oestrogenic substance is of the order of 4:1.

EXAMPLE 6

In the same manner as described in Example 2 two tubes were prepared;

tube I containing a mixture of 98.4% Silastic 382, 0.1% titanium-dioxide and 1.5% 3-keto-desogestrel and tube II containing 96.9 Silastic 382, 0.1% titanium-dioxide, 1.5% ethinyloestradiol and 1.5% of the anti-oestrogenic 3-keto-desogestrel.

With the aid of two glass-plugs of the type as shown in FIG. 1 and silastic medical grade adhesive type A 15 cm of tube I and 1.5 cm of tube II were combined to a vaginal ring-drug delivery system.

The system produces a linear release of 3-keto-desogestrel and ethinyloestradiol in a substantially constant ratio of 7:1.

I claim:

1. A release system for the simultaneous release of two or more active substances, which system consists of two or more reservoirs which each separately contain an active substance and are encased or surrounded by a wall which is permeable to the active substance, the encased reservoirs then being assembled together so that one release system is obtained, characterised in that the said reservoirs are substantially tubular and at least one end of such a tubular reservoir is attached to the end of another tubular reservoir by means of a plug or stopper which does not permit transport of the active substances either by diffusion or by any other method, there being no contact between the walls of the reservoirs involved.

2. Release system according to claim 1, characterised in that two or more reservoirs each containing an active substance, optionally together with a placebo reservoir, are assembled together to form a release system in the shape of a ring.

3. Release system according to claim 2, characterised in that a reservoir containing a progestative substance and a reservoir containing an oestrogenic substance are assembled to form a ring suitable for use as a vaginal ring.

4. Release system according to claim 2, characterised in that one reservoir contains a progestative substance and one reservoir a mixture of an oestrogenic substance and an anti-oestrogenic substance.

* * * * *